(12) United States Patent
Reed et al.

(10) Patent No.: US 11,589,808 B2
(45) Date of Patent: *Feb. 28, 2023

(54) DETECTING CYANIDE EXPOSURE BASED ON THIOCYANATE MEASUREMENT

(71) Applicant: The Government of the United States of America, as represented by the Secretary of Homeland Security, Washington, DC (US)

(72) Inventors: David A. Reed, Baltimore, MD (US); George C. Emmett, Wilmington, DE (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/671,925

(22) Filed: Feb. 15, 2022

(65) Prior Publication Data
US 2022/0167913 A1    Jun. 2, 2022

Related U.S. Application Data

(63) Continuation of application No. 17/246,283, filed on Apr. 30, 2021, now Pat. No. 11,272,878.
(Continued)

(51) Int. Cl.
*A61B 5/1455*    (2006.01)
*A61B 5/00*    (2006.01)
*A61B 10/00*    (2006.01)

(52) U.S. Cl.
CPC ........ *A61B 5/4845* (2013.01); *A61B 5/14551* (2013.01); *A61B 10/0051* (2013.01)

(58) Field of Classification Search
CPC .............. A61B 5/14546; A61B 5/1455; A61B 5/14551; A61B 5/4845; A61B 5/7271
See application file for complete search history.

(56) References Cited

U.S. PATENT DOCUMENTS

| | | | |
|---|---|---|---|
| 3,329,486 | A | 7/1967 | Rupe |
| 5,871,695 | A | 2/1999 | Khartchenko et al. |

(Continued)

FOREIGN PATENT DOCUMENTS

| | | |
|---|---|---|
| CN | 201408184 Y | 2/2010 |
| CN | 110146498 B | 3/2021 |

(Continued)

OTHER PUBLICATIONS

Pena-Pereira et al., "Paper-based analytical device for instrumental-free detection of thiocyanate in saliva as a biomarker of tobacco smoke exposure," Talanta, 147, pp. 390-396, 2016. (Year: 2016).*

(Continued)

*Primary Examiner* — Eric F Winakur
(74) *Attorney, Agent, or Firm* — Lavanya Ratnam; Robert W. Busby; Kelly G. Hyndman

(57) ABSTRACT

In an example, a method of detecting cyanide exposure of an individual comprises measuring a thiocyanate level of the individual, and comparing the measured thiocyanate level to a preset thiocyanate threshold to determine whether the measured thiocyanate level is above the preset thiocyanate threshold indicating a level of cyanide poisoning requiring immediate medical assessment.

31 Claims, 12 Drawing Sheets

Related U.S. Application Data

(60) Provisional application No. 63/036,225, filed on Jun. 8, 2020.

(56) References Cited

U.S. PATENT DOCUMENTS

| | | | |
|---|---|---|---|
| 6,199,550 | B1 | 3/2001 | Wiesmann et al. |
| 6,397,093 | B1 | 5/2002 | Aldrich |
| 6,995,665 | B2 | 2/2006 | Appelt et al. |
| 7,575,553 | B2 | 8/2009 | Stahmann et al. |
| 7,776,610 | B2 | 8/2010 | Carron et al. |
| 7,880,607 | B2 | 2/2011 | Olson et al. |
| 8,741,658 | B2 | 6/2014 | Boss et al. |
| 9,400,284 | B2 | 7/2016 | Vigliotti et al. |
| 10,213,550 | B2 | 2/2019 | Doyle |
| 10,732,098 | B1 | 8/2020 | Soliz et al. |
| 2008/0096281 | A1 | 4/2008 | Geddes et al. |
| 2008/0227746 | A1 | 9/2008 | Boss et al. |
| 2009/0187111 | A1 | 7/2009 | Reilly, Jr. et al. |
| 2010/0291701 | A1 | 11/2010 | Carron et al. |
| 2013/0005044 | A1 | 1/2013 | Boss et al. |
| 2013/0344620 | A1 | 12/2013 | O'Farrell et al. |
| 2020/0265700 | A1 | 8/2020 | Bergman et al. |

FOREIGN PATENT DOCUMENTS

| | | |
|---|---|---|
| WO | 1979000122 A1 | 3/1979 |
| WO | 2009074992 A2 | 6/2009 |
| WO | 2020121276 A1 | 6/2020 |

OTHER PUBLICATIONS

Kirman et al., "Biomonitoring Equivalents for cyanide," Regulatory Toxicology and Pharmacology, 97, pp. 71-81, 2018. (Year: 2018).*
Acute Exposure Guideline Levels for Selected Airborne Chemicals: vol. 2, ISBN: 0-309-56773-4, 292 pages, 6×9, (2002), The National Academies of Sciences Engineering Medicine, The National Academies Press, https://www.nap.edu/catalog/10522/acute-exposure-guideline-levels-for-selected-airborne-chemicals-volume-2.
Taylor, Jessilynn, et al., "Toxicological Profile for Cyanide", U.S. Department Of Health and Human Services Public Health Service, Agency for Toxic Substances and Disease Registry, Atlanta, Georgia, Jul. 2006.
Frederic J. Baud, MD, et al. "Elevated Blood Cyanide Concentrations in Victims of Smoke Inhalation", The New England Journal of Medicine, Dec. 19, 1991.
K. Riedel, et al., "Thiocyanate in plasma and saliva", Analytical Methods, The MAK-Collection Part IV: Biomonitoring Methods, vol. 13, pp. 277-292, 2013.
Rob Schnepp, et al., CPTC Cyanide Poisoning Treatment Coalition, SMOKE Cynaide and Carbon Monoixde: The Toxic Twins of Smoke Inhalation_vol. 2, Mar. 2009, Indianapolis, IN.
Jeremy T. Cushman et al., Smoke Inhalation and Management, University of Rochester, Division of PreHospital Medicine, Aug. 2014 accessed online May 20, 2019.
Marc Eckstein et al., "Focus on Smoke Inhalation—The Most Common Cause of Acute Cyanide Poisoning", Prehospital and Disaster Medicine, vol. 21, No. 2, Mar. 23, 2006.
Ben Evarts, et al., United States Firefighter Injuries 2017_Nov. 2018 Nation Fire Protection Association, NFPA Research, Quincy MA.
Eike Hamad et al., Case Files of the University of Massachusetts Toxicology Fellowship: Does This Smoke Inhalation Victim Require Treatment with Cyanide Antidote, J. Med Toxicol., DOI 10.1007/s13181-016-0533-0, American College of Medical Toxicology, published online: Feb. 1, 2016, 12: pp. 192-198.
Inchem,_"Hydrogen Cyanide and Cyanides Human Health Aspects", Cicads 61, Geneva, 2004, http://www.inchem.org/documents/cicads/cicads/cicad61.htm.
Amal Jubran, "Pulse Oximetry", Critical Care, 19:272, Jul. 16, 2015, DOI 10.1186/s13054-015-0984-8.
Kamonwad Ngamchuea et al., Chemical analysis in saliva and the search for salivary biomarkers—a tutorial review, Analyst, 143, pp. 81-99, The Royal Society of Chemistry, (2018).
Markku Lahti et al., "Spectrophotometric Determination of Thiocyanate in Human Saliva", Journal of Chemical Education, vol. 76, No. 9, Sep. 1999.
Marshal S. Levin, M.D., M.P.H. and Edward P. Radford, M.D.; "Occupational Exposures to Cyanide in Baltimore Fire Fighters", Journal of Occupational Medicine, vol. 20, No. 1, Jan. 1978.
Inna Leybell, "Cyanide Toxicity Workup: Approach Considerations", Medscape, Jan. 2, 2018.
Micha Y. Shamir et al., "The Current Status of Continuous Noninvasive Measurement of Total, Carboxy, and Methemoglobin Concentralion", Anesthesia and Analgesia, vol. 114, No. 5, pp. 972-978, May 2012.
Brian A. Logue et al., U.S. Army Medical Research Institute of Chemical Defense, "The Analysis of Cyanide and its Breakdown Products in Biological Samples", Critical Reviews in Analytical Chemistry, 40: pp. 122-147, 2010.
NASEMSO National Model EMS Clinical Guidelines, Version 2.2, Jan. 5, 2019, NASEMSO Medical Directors Council, www.nasemso.org.
National Fire Protection Association, "Reporter's Guide: The consequences of fire", https://www.nfpa.org/News-and-Research/Publications-and-media/Press, accessed on Jul. 10, 2019.
Oswego Firefighters become first in CNY to offer life-saving pre-hospital cyanide antidote, http://www.oswegocountynewsnow.com/news/oswego-firefighters-become-first-in-cny-to-offer-life-saving/article_13eee1a8-98ea-11e9-a0fb-6701e674df9f.html, accessed on Jun. 28, 2019.
Y. Saloojee et al.,"Carboxyhaemoglobin and plasma thiocyanate: complementary indicatiors of smoking behaviour?", Thorax, 37: 521-525, Jul. 1, 1982.
I.S. Symington et al., "Cyanide Exposure In Fires", The Lancet, vol. 2, Issue 8080, pp. 91-92, Jul. 8, 1978.
Steven I. Baskin et al., "Cyanide Poisoning", Medical Aspects of Chemical Warfare, Textbook of Military Medicine, Chapter 11, pp. 371-410, 2008.
Kouichiro Tsuge et al., "Cyanide and Thiocyanate Levels in Blood and Saliva of Healthy Adult Volunteers", Journal of Health Science vol. 46(5) pp. 343-350 (2000).
Curtis Varone, "Cyanide Poisoning: How Much Of A Threat?", Fire Engineering, Sep. 1, 2006, Fire Engineering, https://www.fireengineering.com/articles/print/volume-159/issue-9/.

* cited by examiner

Table 1. Preparation of Standard Solutions for Determination of ε of FeSCN$^{2+}$ Complex

| Test Tube No. | Volume/mL | | |
|---|---|---|---|
| | Fe(NO$_3$)$_3$ 0.200 M | KSCN 2.00×10$^{-4}$ M | H$_2$O |
| 0 | 5 | 0 | 5 |
| 1 | 5 | 1 | 4 |
| 2 | 5 | 2 | 3 |
| 3 | 5 | 3 | 2 |
| 4 | 5 | 4 | 1 |
| 5 | 5 | 5 | 0 |

Table 2. Measurements of Saliva Thiocyanate Concentration

| Range/mM | Group | | |
|---|---|---|---|
| | Nonsmokers (No.) | Smokers (No.) | All (No.) |
| 0.4–1.0 | 25 | 0 | 25 |
| 1.1–2.0 | 71 | 5 | 76 |
| 2.1–3.0 | 31 | 3 | 34 |
| 3.1–4.0 | 7 | 1 | 8 |
| 4.1–5.0 | 1 | 2 | 3 |
| 5.1–5.6 | 0 | 1 | 1 |
| Total | 135 | 12 | 147 |

FIG. 2

Table 3
Average Cyanide and Thiocyanate Levels (μM) in Blood and Salivary Samples Taken from Healthy Volunteers[a]

|  | Total | Nonsmoker | Smoker | 1-5[a] | 6-10 | 11-20[a] | 21 >[a] |
|---|---|---|---|---|---|---|---|
| Number of subjects | 40 | 20 | 20 | 1 | 2 | 3 | 14 |
| Blood cyanide | 0.22 ± 0.08 | 0.17 ± 0.04 | 0.27 ± 0.07[b] | 0.18 | 0.20 ± 0.06 | 0.26 ± 0.02[b] | 0.29 ± 0.06[b] |
| Plasma Thiocyanate | 72.4 ± 77.4 | 33.5 ± 25.4 | 111.2 ± 92.1[b] | 5.7 | 54.7 ± 53.0 | 76.0 ± 55.8 | 134.4 ± 96.3[b] |
| Salivary Cyanide | 0.52 ± 0.42 | 0.38 ± 0.26 | 0.66 ± 0.52[c] | 0.22 | 0.62 ± 0.05[b] | 0.51 ± 0.54 | 0.72 ± 0.57[c] |
| Salivary Thiocyanate | 1098 ± 862 | 542 ± 406 | 1655 ± 841[b] | 899 | 432 ± 155 | 1858 ± 672[b, d] | 1840 ± 801[b, d] | a) Number of cigarettes smoked per day.
b) Significantly higher (p < 0.01) compared to the nonsmoker group.
c) Significantly higher (p < 0.05) compared to the nonsmoker group.
d) Significantly higher (p < 0.01) compared to the smoker group who have smoked 6-10 cigarettes per day.

FIG. 3

| Table 4 | Thiocyanate levels in plasma and saliva of non-smokers and smokers (MV ± SD). | | |
|---|---|---|---|
| Non-smokers | | Smokers | Reference |
| Thiocyanate in plasma (mg/L) | | | |
| 3.47 ± 2.39 (n = 6815) | | 9.09 ± 3.41 (n = 10377) | Bliss and O'Connell, 1984 [11] |
| 3.16 ± 1.75 (n = 1356) | | 10.10 ± 3.22 (n = 5090) | Ockene et al., 1987 [12] |
| 3.08 ± 1.59 (n = 3274) | | 10.04 ± 3.03 (n = 4553) | Ruth and Neaton, 1991 [13] |
| Thiocyanate in saliva (mg/L) | | | |
| 70.9 ± 44.2 (n = 242) | | 158 ± 64.5 (n = 287) | Bliss and O'Connell, 1984 [11] |
| 75.5 (n = 100) | | 142 (n = 94) | Jarvis et al., 1984 [14] |
| 97.0 (median) (n = 207) | | 170 (median) (n = 117) | Degiampietro et al., 1987 [1] |

FIG. 4

Scatter diagram of carboxyhaemoglobin (COHb) v thiocyanate (SCN) values in 439 adults with the line of discrimination between smokers (□) and non-smokers (×). The dashed lines are the limiting values of 1·6% COHb and 73 μmol SCN/L.

ENDOGENOUS CYANIDE CONCENTRATIONS FOR SMOKERS AND NONSMOKERS[*]

| | Cyanide | | | | | | | |
|---|---|---|---|---|---|---|---|---|
| | Nonsmokers | | | | Smokers | | | |
| Subsample Size in Study | Whole Blood (ng/mL) | Erythrocytes (ng/mL) | Plasma (ng/mL) | Saliva (ng/mL) | Whole Blood (ng/mL) | Erythrocytes (ng/mL) | Plasma (ng/mL) | Saliva (ng/mL) |
| n=20[a] | 4.4 ± 1.0 | | | | 7.0 ± 1.8 | | | 17.1 ± 13.5 |
| n=5 smokers; n=10 nonsmokers[c] | 3.5 ± 2.1 | 6.5 ± 5.9 | 0.54 ± 0.54 | 9.9 ± 6.8 | 8.9 ± 3.2 | 18.0 ± 5.4 | 0.81 ± 0.54 | |
| n=10 nonsmokers[b] | 51.3 ± 17.3 | | | | | | | |

| | Thiocyanate | | | |
|---|---|---|---|---|
| | Whole Blood (ng/mL) | Plasma (ng/mL) | Urine (ng/mL) | Saliva (ng/mL) | Whole Blood (ng/mL) | Plasma (ng/mL) | Urine (ng/mL) | Saliva (ng/mL) |
| n=20[a] | 1.94 ± 1.47 | | | 31.4 ± 23.5 | 6.54 ± 5.34 | | | 96.0 ± 48.8 |

| | 2-Aminothiazoline-4-carboxylic Acid | | |
|---|---|---|---|
| | Whole Blood (ng/mL) | Plasma (ng/mL) | | | Whole Blood (ng/mL) | Plasma (ng/mL) | | |
| n=10 smokers; n=21 nonsmokers[d] | | 85 ± 47 | | | | 233 ± 237 | | |
| n=27 smokers; n=27 nonsmokers[e] | 11.8 ± 4.7 | | | | 17.2 ± 3.2 | | | |

Table 5

FIG. 7

DETECTING CYANIDE EXPOSURE BASED ON THIOCYANATE MEASUREMENT

CROSS-REFERENCE TO RELATED APPLICATIONS

The application is a continuation of U.S. patent application Ser. No. 17/246,283, filed Apr. 30, 2021, entitled SYSTEM AND METHOD FOR DETECTING CYANIDE EXPOSURE, which is a nonprovisional of and claims the benefit of priority from U.S. Provisional Patent Application No. 63/036,225, filed on Jun. 8, 2020, entitled SYSTEM AND METHOD FOR DETECTING CYANIDE EXPOSURE, the entire disclosures of which are incorporated by reference.

STATEMENT OF GOVERNMENT INTEREST

This invention was made with Government support, provided by the United States Department of Homeland Security, via DTIC contract FA8075-14-D-0003, and by an employee of the United States Department of Homeland Security in the performance of their official duties. The U.S. Government has certain rights in this invention.

FIELD

The discussion below relates generally to systems and methods of detecting chemical exposure and, more particularly, to the detection of cyanide exposure.

BACKGROUND

On average, each year more than 3,000 Americans die and more than 14,000 are injured as a result of injuries sustained from fires in the United States. In 2017, for instance, there were 1,319,500 fires in the United States, approximately 30% of which were residential and non-residential building fires. There were 14,670 injuries and 3,400 deaths with most of both categories resulting from smoke inhalation. In addition, 4,510 firefighters were reported as being injured by smoke inhalation, 550 suffered heart attacks, and 850 had other respiratory distress. Of the 550 heart attacks, 50 fatalities were reported. Only recently has the medical community understood the consequences of cyanide poisoning associated with building fires and the need to address this potential threat. The most common cause of death in fires is the inhalation of noxious gases rather than thermal injury. Hydrogen cyanide gas, the most toxic product of combustion, seldom was recognized as a significant hazard in smoke inhalation. Even the most heroic efforts were ineffective if life-saving oxygen is blocked from the cells by cyanide.

Although cyanide is suspected of playing a role in smoke inhalation injury and death, definitive correlations of the role of cyanide have not been made because of the complex nature of fire smoke toxins and exposure. Nonetheless, that cyanide exposure has been a factor in fatalities is established. Cyanide intoxication can lead to death by ceasing cellular respiration or contributing to a heart attack.

One of the challenges with cyanide poisoning is that it is hard to measure in an exposed individual. Timely administration of the antidote is important to treat the exposed individual, but the high cost of treatment renders it difficult to justify its use without more reliable proof that the individual is indeed suffering from cyanide poisoning.

SUMMARY

Embodiments of the present invention are directed to a fast, on-scene test for presumptively identifying if a smoke exposed person has inhaled a dangerous amount of cyanide gas. Carbon monoxide (CO) and hydrogen cyanide (HCN) are the toxic twins of smoke inhalation. In one example, detection of intoxication by CO can be performed quickly and easily on-site with a modern pulse oximeter.

Heretofore, there has been no widely available, affordable, rapid, confirmatory cyanide exposure test such as a cyanide blood test. Assessment of cyanide exposure levels is difficult. Detection of cyanide exposure is not performed by instrument. Firefighters and medical personnel are trained to watch for signs and symptoms of cyanide exposure, but this can be problematic since many cyanide/HCN physical indicators are similar to, or disguised by, CO signs and symptoms. Cyanide intoxication can be treated. Responders have to rely on getting the exposed individual to the hospital for treatment where treatment decisions are made on the basis of clinical history and signs and symptoms of cyanide intoxication.

While detection of cyanide in blood is difficult, it is possible to detect thiocyanate in saliva. Thiocyanate is formed as a direct response of the body to detoxify cyanide, which is a naturally occurring substance and relatively harmless in normal dietary amounts. In addition, the presence of methemoglobin, which captures and temporarily holds some of the cyanide, in an individual may suggest that little or no free cyanide is available for binding. A substantial reduction of the methemoglobin in a cyanide exposed individual may indicate that the capacity for conversion to thiosulfate has been exceeded. While a significantly elevated salivary thiocyanate above a threshold level is believed to be a sufficient basis to indicate that the main cyanide detoxification mechanisms have been overwhelmed in a cyanide exposed individual, a combination of elevated salivary thiocyanate and depressed methemoglobin values may provide an even stronger basis by taking into account variations in endogenous cyanide levels in different individuals. Measuring these two parameters could provide a more reliable screening method for cyanide intoxication.

In one embodiment a screening method for cyanide intoxication is based on measuring the presence or absence of elevated salivary thiocyanate and depressed methemoglobin values. First, a screening test for high thiocyanate levels is possible based on the reaction with iron nitrate. For instance, the exposed individual can have a saliva sample taken and contacted with a sample collection device (e.g., a swab or a strip) with a colorimetric indicator such as iron nitrate to indicate high thiocyanate levels in saliva. Second, pulse oximetry can measure low methemoglobin to indicate that methemoglobin is no longer available to bind with cyanide. A substantial reduction of methemoglobin in a cyanide exposed individual indicates that the capacity for conversion to thiosulfate has been exceeded. It is believed that high salivary thiocyanate levels will presumptively indicate that a toxic exposure to cyanide has occurred. Methemoglobin levels may add further confirmation or refinement to determining a level of salivary thiocyanate that indicates further medical treatment or screening is needed. Pulse oximetry can also measure carboxyhemoglobin to assess the exposure to CO which could adjust the danger level of cyanide exposure. In another embodiment, the first measurement alone may be adequate to indicate that the natural detoxification methods in the body are overwhelmed.

In one example, a saliva sample from a potentially exposed person can be placed in contact with a simple chemical indicator that will indicate, in conjunction with pulse oximetry measurements, whether or not a high-level cyanide exposure has occurred. Now victims of building fires and hazardous materials incidents can experience the benefits of an antidote sooner. This invention will likely save lives, since the single most important factor driving successful conversion of a potentially lethal exposure of cyanide into full recovery is timeliness of rescue.

In accordance with an aspect of the present disclosure, a method of detecting cyanide exposure of an individual comprises measuring a thiocyanate level of the individual, and comparing the measured thiocyanate level to a preset thiocyanate threshold to determine whether the measured thiocyanate level is above the preset thiocyanate threshold indicating a level of acute cyanide poisoning for which medical treatment is recommended to treat health effects of the exposure.

In accordance with another aspect of the disclosure, a method of detecting cyanide exposure of an individual, the method comprising: measuring a thiocyanate level of the individual; comparing the measured thiocyanate level to a first preset thiocyanate threshold to determine whether the measured thiocyanate level is above the first preset thiocyanate threshold; if the measured thiocyanate level is above the first preset thiocyanate threshold, recommending further medical assessment possibly leading to treatment to treat health effects of the exposure; if the measured thiocyanate level is not above the first preset thiocyanate threshold, then performing at least one of the following two processes. The first process includes measuring a methemoglobin level of the individual, comparing the measured thiocyanate level to a second preset thiocyanate threshold, which is lower than the first preset thiocyanate threshold, to determine whether the measured thiocyanate level is above the second preset thiocyanate threshold, comparing the measured methemoglobin level to a preset methemoglobin threshold to determine whether the measured methemoglobin level is below the preset methemoglobin threshold, and if the measured thiocyanate level is above the second preset thiocyanate threshold and the measured methemoglobin level is below the preset methemoglobin threshold, recommending medical treatment to treat health effects of the exposure. The second process includes measuring a carboxyhemoglobin level of the individual, comparing the measured thiocyanate level to a third preset thiocyanate threshold, which is lower than the first preset thiocyanate threshold, to determine whether the measured thiocyanate level is above the third preset thiocyanate threshold, comparing the measured carboxyhemoglobin level with a preset carboxyhemoglobin threshold to determine whether the measured carboxyhemoglobin level is above the preset carboxyhemoglobin threshold, and if the measured thiocyanate level is above the third preset thiocyanate threshold and the measured carboxyhemoglobin level is above the preset carboxyhemoglobin threshold, recommending medical treatment to treat health effects of the exposure.

In accordance with another aspect of this disclosure, a method of detecting cyanide exposure of an individual comprises: determining a preset thiocyanate threshold; measuring a thiocyanate level of the individual; and comparing the measured thiocyanate level to the preset thiocyanate threshold to determine whether the measured thiocyanate level is above the preset thiocyanate threshold indicating a level of acute cyanide poisoning for which medical treatment is recommended to treat health effects of the exposure. Determining the preset thiocyanate threshold includes: measuring thiocyanate levels of a plurality of unexposed individuals who have not been exposed to cyanide; measuring thiocyanate levels of a plurality of exposed individuals after an exposure of the plurality of exposed individuals to cyanide; monitoring the plurality of exposed individuals after the exposure for health effects of the exposure; identifying, out of the plurality of exposed individuals being monitored, one or more harmed individuals for whom medical treatment is recommended to treat the health effects of the exposure; comparing the thiocyanate levels of the plurality of unexposed individuals, the thiocyanate levels of the one or more harmed individuals, and the thiocyanate levels of the plurality of exposed individuals after the exposure who are not the one or more harmed individuals; determining, based on the comparing, a threshold thiocyanate level above which medical treatment is recommended to treat the health effects of the exposure; and setting the threshold thiocyanate level as the preset thiocyanate threshold.

Other features and aspects of various examples and embodiments will become apparent to those of ordinary skill in the art from the following detailed description which discloses, in conjunction with the accompanying drawings, examples that explain features in accordance with embodiments. This summary is not intended to identify key or essential features, nor is it intended to limit the scope of the invention, which is defined solely by the claims.

BRIEF DESCRIPTION OF THE DRAWINGS

The attached drawings help explain the embodiments described below.

FIG. 2 includes two tables. Table 1 shows preparation of standard solutions for determination of the molar absorption coefficient of $FeSCN^{2+}$ complex. Table 2 shows measurement of saliva thiocyanate concentration.

FIG. 3 includes Table 3 which shows average cyanide and thiocyanate levels ($\mu M$) in blood and salivary samples taken from healthy volunteers.

FIG. 4 includes Table 4 which shows thiocyanate levels in plasma and saliva of nonsmokers and smokers (MV±SD).

FIG. 7 includes Table 5 which lists reported endogenous concentrations of cyanide in various biological samples from human smokers and non-smokers.

DETAILED DESCRIPTION

Figure 1:
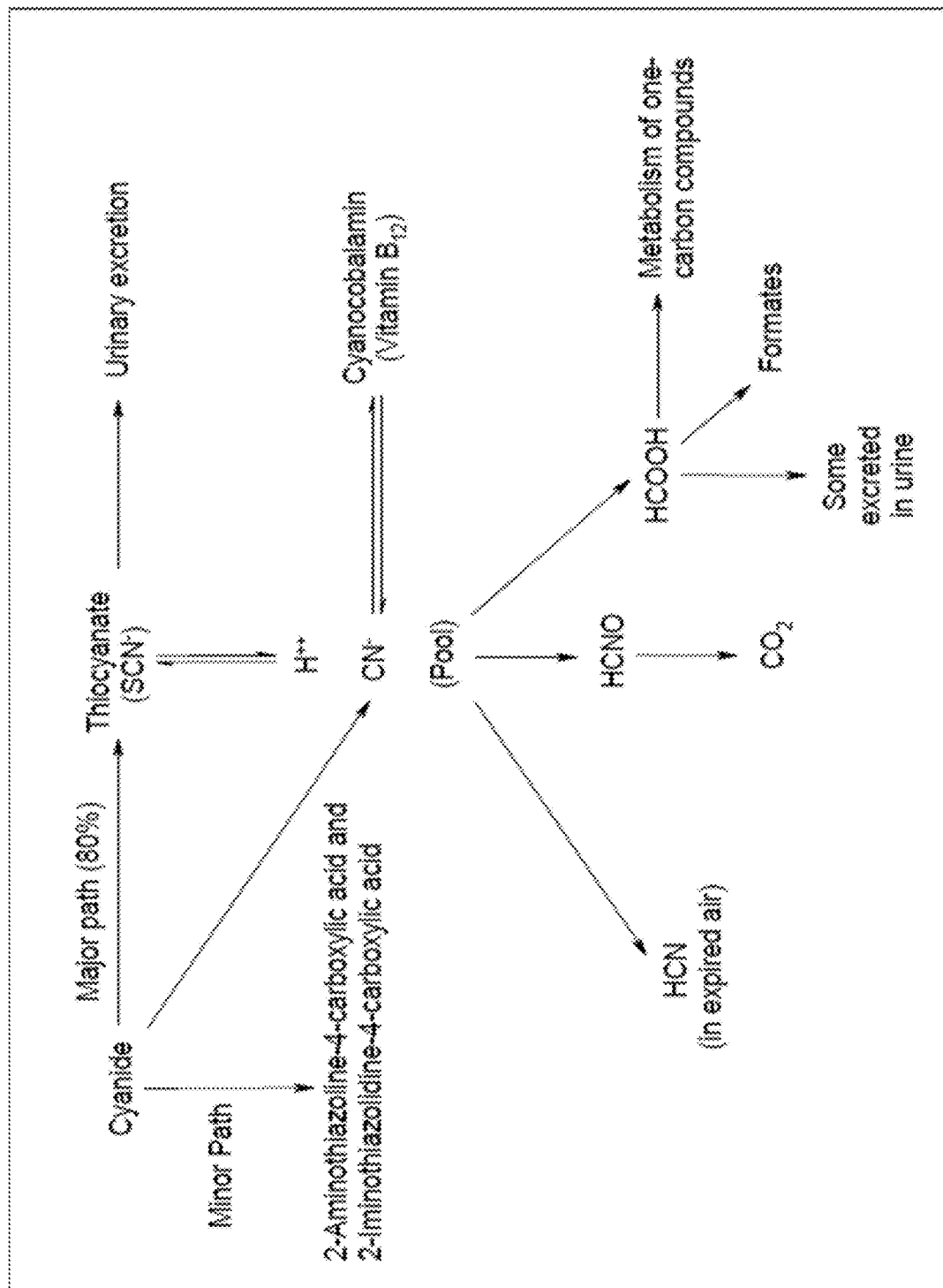
FIG. 1 shows the cyanide metabolism after it enters the bloodstream.

A number of examples or embodiments of the present invention are described, and it should be appreciated that the present invention provides many applicable inventive concepts that can be embodied in a variety of ways. The embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure along with the knowledge of one of ordinary skill in the art.

In firefighting, CO is generally the more prevalent substance found in residential fires, but cyanide is much more toxic. Both CO and cyanide inhibit the use of oxygen by cells: CO by blocking adsorption of oxygen by hemoglobin and cyanide by blocking cellular respiration. The effects of these two gasses are thought to be additive and fatalities have occurred with less than fatal levels of each substance alone. Rapid on-site detection of health threatening exposure is limited to CO, via the formation of carboxyhemoglobin, pulse oximetry. Detection of HCN exposure cannot be easily, or quickly, performed and is recommended to be done by observation of potential victim's signs and symptoms.

Cyanide is suspected of playing a role in heart attacks. It is known to cause heart arrhythmias but direct connection to cyanide exposure has not been firmly correlated to a fire smoke environment. Furthermore, other heart stressors such as CO and particulate exist in a fire smoke environment.

Cyanides are well absorbed via the gastrointestinal tract or skin and rapidly absorbed via the respiratory tract. Once absorbed, cyanide is rapidly and ubiquitously distributed throughout the body, although the highest levels are typically found in the liver, lungs, blood, and brain. There is no accumulation of cyanide in the blood or tissues following chronic or repeated exposure.

Approximately 80% of absorbed cyanide is initially metabolized to thiocyanate in the liver by the mitochondrial sulfur transferase enzyme rhodanese and other sulfur transferases. Thiocyanate is excreted in the urine. Minor pathways for cyanide detoxification involve reaction with cystine to produce aminothiazoline-carboxylic and iminothiazolidinecarboxylic acids and combination with hydroxycobalamin (vitamin $B_{12a}$) to form cyanocobalamin (vitamin $B_{12}$); these end-products are also excreted in the urine. See FIG. 1.

Cyanide is naturally occurring and mechanisms to cope with cyanide exposure already exist within the body. The major route is formation of thiocyanate until the sulfur donors are depleted. Thiocyanate ($SCN^-$) is relatively non-toxic and concentrates in the saliva. It is more stable in the blood stream but variable between person to person. Studies have demonstrated that smokers can be distinguished from non-smokers by salivary $SCN^-$. Only when the detoxification mechanisms are overwhelmed does serious injury from cyanide begin. Cyanide and cyanide detoxification chemicals show up in red blood cells, blood plasma, saliva, and urine. These mechanisms can provide the information that tells what level of cyanide is in the body.

FIG. 1 shows the cyanide metabolism after it enters the bloodstream. ATSDR, Toxicological Profile for Cyanide (July 2006). The major detoxification route for cyanide is conversion to the less toxic thiocyanate ($SCN^-$) catalyzed by the enzyme rhodanese. Animal studies indicate that this is the major metabolic pathway for cyanide detoxification with about 80% of the initial cyanide exposure converted to thiocyanate:

This causes a spike in blood thiocyanate levels. Conversion, however, is limited by the amount of sulfur donors, mainly thiosulfate, available. One medical treatment method for cyanide exposed individuals includes administration of sodium thiosulfate to boost sulfur donors. A second mechanism for cyanide detoxification occurs when cyanide in the red blood cells binds with methemoglobin, to form cyanomethemoglobin, which is relatively non-toxic and holds the cyanide for eventual elimination through the thiocyanate pathway. Methemoglobin is normally between 0.25% and 1% of hemoglobin and, at normal levels, can bind approximately 10 mg of cyanide. Another medical treatment method for cyanide exposure is administration of amyl nitrate, or similar compound, which increases blood methemoglobin. Through the detoxification mechanisms, the rate of detoxification of HCN in humans may be about 0.017 mg CN/kg*min as reported by McAllister citing Ballantyne in McAllister et al., Stability of CN in cadavers J. Anal. Tox. 2008, or about 1 mg CN/kg/Hr as reported by Ketha and Garg in Hema Ketha, Uttam Garg. Toxicology Cases for the Clinical and Forensic Laboratory, Academic Press 2020, accessed Apr. 1, 2021, http://search.ebscohost.com/login.aspx?direct=true&db=nlebk&AN=2226023 & site=eds-live.

Pulse oximetry, the measurement of transmission of specific light frequencies across the finger or earlobe, has advanced to point where detection of oxyhemoglobin, reduced hemoglobin (deoxygenated hemoglobin), methemoglobin, and carboxyhemoglobin are routinely performed. Carboxyhemoglobin is especially critical as it is the toxic actor for CO poisoning. In the future, it may be possible to use pulse oximetry, or related technology, to measure cyanomethemoglobin; however, it is likely that difficulties in concentration, pulse oximeters measure constituents as a percentage where cyanide components exist at the micro molar range, and interference from other substances, have prevented this from reaching the marketplace to date. As a result, cyanide intoxication is usually diagnosed clinically based on signs and symptoms because clinical test results may not be available for hours or days.

Measurement of the methemoglobin level is especially important in cyanotic patients. The presence of methemoglobin suggests that little or no free cyanide is available for binding because methemoglobin vigorously binds cyanide to form cyanomethemoglobin (which is not measured by pulse oximetry as methemoglobin). A substantial reduction of the methemoglobin in a cyanide exposed individual could indicate that the capacity for conversion to thiosulfate has been exceeded.

The levels of cyanide and thiocyanate have been reported for smokers, non-smokers, firefighters, and victims. The reporting reveals that salivary thiocyanate levels show a very large range between subjects, but the levels in saliva are much higher than cyanide or thiocyanate levels in other biological fluids. FIG. 2 includes two tables. Table 1 shows preparation of standard solutions for determination of the molar absorption coefficient ε of $FeSCN^{2+}$ complex. Six solutions in test tubes were prepared for the determination of ε of $FeSCN^{2+}$ complex according to Table 1. Table 2 shows measurement of saliva thiocyanate concentration. The qualitative and quantitative analysis of thiocyanate ion in human saliva was performed as a part of the exercise to determine the chemical equilibrium between $Fe^{3+}$ and $SCN^-$ ions. The results are collected in Table 2. The saliva thiocyanate ion concentration of 147 subjects varied from 0.4 to 5.6 mM. It is clearly demonstrated that cigarette smokers (ca. 10%) tend to have higher $SCN^-$ concentration than the nonsmokers.

Tables 1 and 2 are disclosed in Lahti et. al., Spectrophotometric Determination of Thiocyanate in Human Saliva, J. Chemical Education, Vol. 76, No. 9, 1281-82 (1999).

FIG. 3 includes Table 3 which shows average cyanide and thiocyanate levels (04) in blood and salivary samples taken from healthy volunteers. The salivary cyanide levels in the smokers are significantly higher than those in the nonsmokers. Table 3 is disclosed in Tsuge et al., Cyanide and Thiocyanate Levels in Blood and Saliva of Healthy Adult Volunteers, J. Health Science 46(5) 343-350 (2000). FIG. 4 includes Table 4 which shows thiocyanate levels in plasma and saliva of nonsmokers and smokers (MV±SD). Compared with non-smokers, smokers show 2 to 3 times higher thiocyanate levels. Table 4 is disclosed in Biomonitoring Methods Thiocyanate in Plasma and Saliva, MAK Collection, Vol. 13 (2013).

Figure 5:
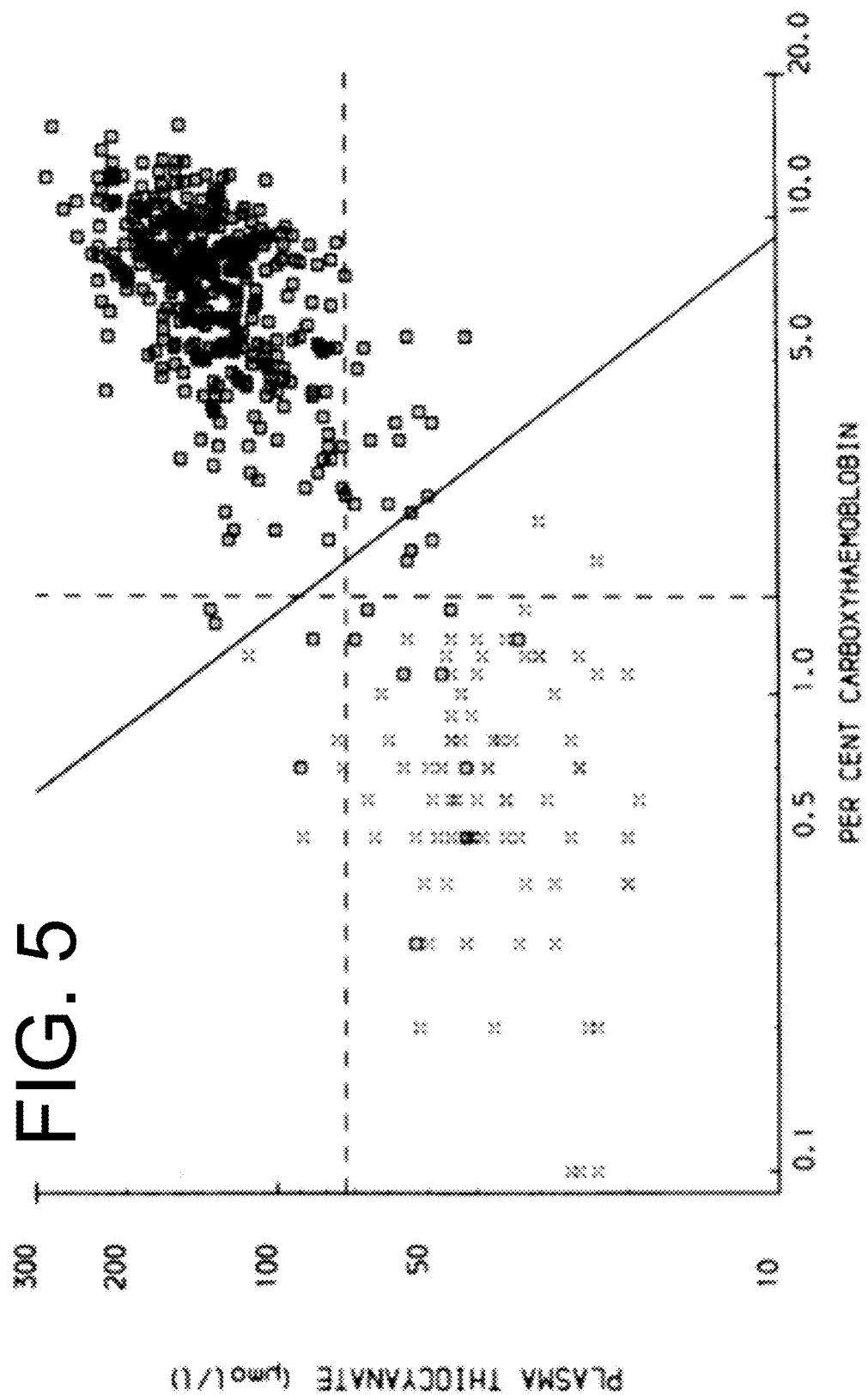
FIG. 5 shows a scatter diagram of carboxyhemoglobin (COHb) versus thiocyanate ($SCN^-$) values in 439 adults with the line of discrimination between smokers and nonsmokers.

Carboxyhemoglobin and plasma thiocyanate concentrations were measured in 79 non-smokers and 360 cigarette smokers in the study by Soloojee et. al., Carboxyhemoglobin and plasma thiocyanate complementary indicators of smoking behavior, Thorax 37, 521-525 (1982). FIG. 5 is disclosed in Soloojee et al. and shows a scatter diagram of carboxyhemoglobin (COHb) versus thiocyanate ($SCN^-$) values in 439 adults with the line of discrimination between smokers and non-smokers. The dashed lines are the limiting values of 1-6% COHb and 73 μmol $SCN^-$/l. Based on FIG. 5, it appears that plasma offers the best differentiation between thiocyanate concentrations found in smokers and non-smokers.

Figure 6:
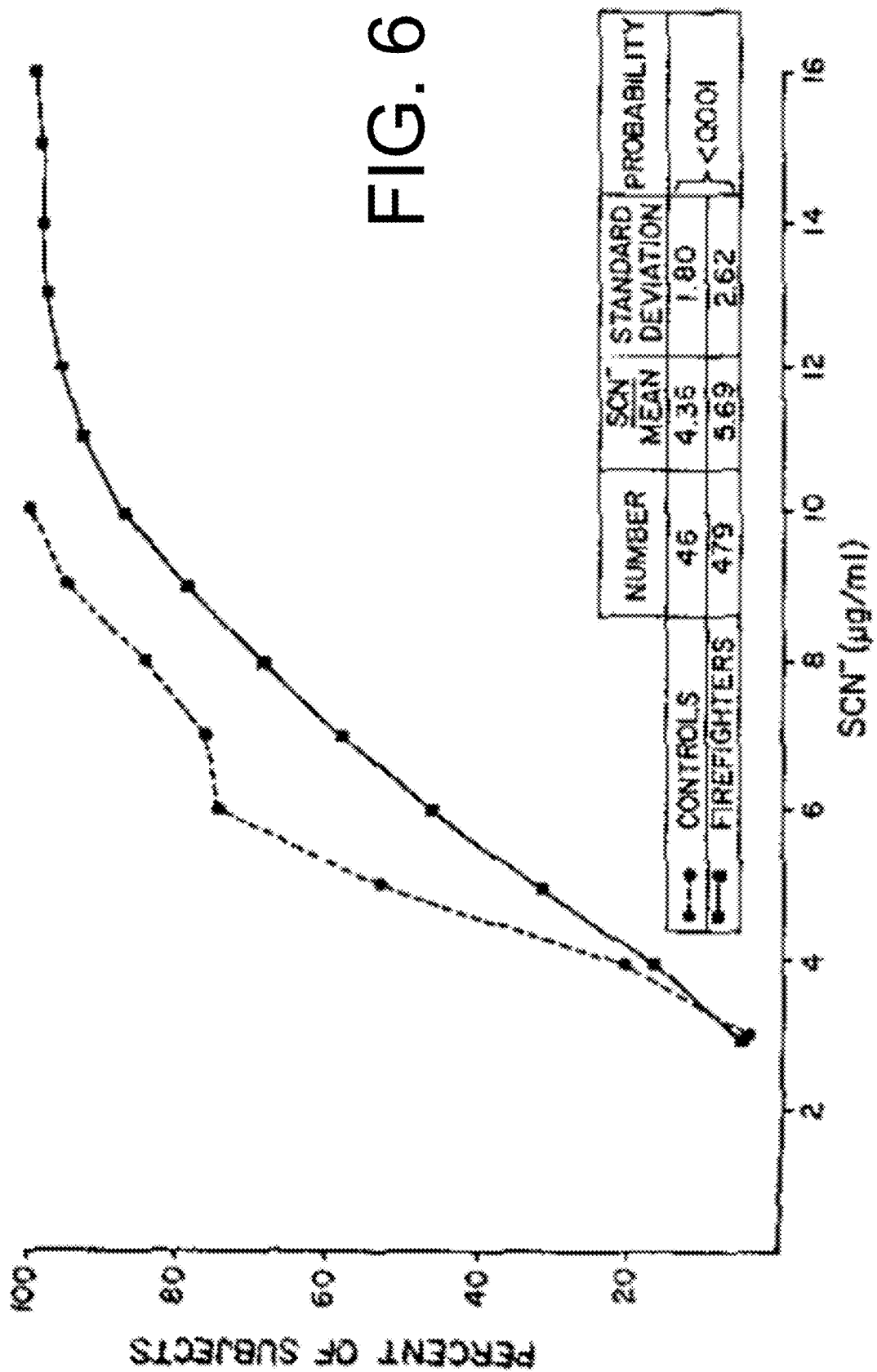
FIG. 6 shows serum thiocyanate levels in nonexposed control subjects compared to exposed firefighters (all smoking categories).

The relationship of thiocyanate with fire smoke exposure can be inferred from a 1973/74 study of Baltimore firefighters. Serum thiocyanate was measured from blood samples drawn from firefighters on-site immediately after the firefighter left the fire atmosphere. Maximum serum thiocyanate was highest for the firefighters regardless of smoking categories; however, some exposed firefighters had lower levels than control subjects. FIG. 6 shows serum thiocyanate levels in nonexposed control subjects compared to exposed firefighters (all smoking categories). FIG. 6 is disclosed in Levin and Radford, Occupational Exposures to Cyanide in Baltimore Fire Fighters, J. Occupational Medicine, Vol. 20, No. 1 (January 1978). For that study, no firefighter was reported as suffering from cyanide intoxication indicating that the levels reported, though high, might not be as high as a presumptive screening test would need to be.

Comparing FIG. 4 to FIG. 6, one can see that the thiocyanate ($SCN^-$) in plasma shown in FIG. 4 compares well to the controls in FIG. 6 (a ug/ml=mg/l). FIG. 4 shows corresponding salivary thiocyanate levels 15 to 20 times higher, which makes detection easier.

Thiocyanate (rhodanide) is the main metabolite of cyanide and can thus be used as biomarker for exposure to cyanide or to cyanide releasing chemicals. Especially for chronic exposure to low cyanide concentrations (e.g., exposure from smoking or at certain workplaces), thiocyanate in plasma and saliva is a suitable biomarker. An aspect of the detection methodology is based on the rapid and reliable determination of thiocyanate in saliva using a photometric method. When Fe(III) ions are added to samples containing thiocyanate, a red complex is formed, which is measured close to its absorption maximum at 492 nm.

The photometric method permits the quantitative determination of thiocyanate in small sample volumes and with a short sample preparation time. One approach uses a plate reader by adaption to microtiter plates and is particularly suitable for the determination of large sample numbers. The thiocyanate levels in saliva are approximately 20 times higher than the corresponding levels in plasma (see Table 4 in FIG. 4). This is probably due to active secretion of the thiocyanate ion via the salivary glands. Furthermore, thiocyanate concentrations in saliva strongly depend on salivary flow. For this reason, thiocyanate levels in saliva are, despite better precision, subjected to greater intra-individual variations than thiocyanate levels in plasma. Owing to the long half-life of thiocyanates, i.e., 6-14 days, this biomarker ought to be especially suitable for determining chronic exposures to low cyanide concentrations. For the given reasons, this at least applies to thiocyanate in saliva to a limited extent.

Various cyanide detection scheme candidates are considered. In terms of arterial and venous blood gases, cyanide toxicity is characterized by a normal arterial oxygen tension and an abnormally high venous oxygen tension, resulting in a decreased arteriovenous oxygen difference (<10%). A high-anion-gap metabolic acidosis is a hallmark of significant cyanide toxicity. Apnea may result in combined metabolic and respiratory acidosis. In terms of blood lactate level, elevation in the blood lactate level is a sensitive marker for cyanide toxicity. A plasma lactate concentration of greater than 10 mmol/L in smoke inhalation or greater than 6 mmol/L after reported or strongly suspected pure cyanide poisoning suggests significant cyanide exposure. With regard to red blood cell or plasma cyanide concentration, cyanide blood concentrations are not generally available in time to aid in the treatment of acute poisoning but may provide subsequent confirmation. In cyanogen exposures, these tests provide documentation for therapeutic use, which may last several days. The preferred test is a red blood cell cyanide concentration. With this method, mild toxicity is observed at concentrations of 0.5-1.0 μg/mL. Concentrations of 2.5 μg/mL and higher are associated with coma, seizures, and death. Blood cyanide concentrations may artificially increase after sodium nitrite (antidote) administration, because of in vitro release of cyanide from cyanomethemoglobin during the analytical procedure by strong acid used in analysis.

Because CO and HCN are the toxic twins of smoke inhalation, detection of CO poisoning is part of the present methodology. One approach is based on measuring carboxyhemoglobin level to determine blood carbon monoxide concentration. Carboxyhemoglobin (HbCO) level (by co-oximetry) or blood carbon monoxide concentration (by infrared spectroscopy) may be obtained in patients with smoke inhalation to rule out concurrent exposure. HbCO measurements may be artificially elevated in blood samples drawn after hydroxocobalamin administration.

The chosen candidate involves the detection of a methemoglobin level, which is especially important in cyanotic patients. The presence of methemoglobin suggests that little or no free cyanide is available for binding because methemoglobin vigorously binds cyanide to form cyanomethemoglobin (which is not measured as methemoglobin by pulse oximetry). Methemoglobin concentrations provide a guide for continued therapy after the use of methemoglobin inducing antidotes, such as sodium nitrite. Elevated levels of methemoglobin (>10%) indicate that further nitrite therapy is not indicated and, in fact, may be dangerous.

When analyzing for cyanide exposure, it is important to note that all biological samples will contain endogenous levels of cyanide (and its biological markers). Therefore, baseline levels of the analyte (cyanide, thiocyanate, ATCA, or cyanide-protein adducts) should be known prior to concluding the occurrence of a cyanide exposure. FIG. 7 includes Table 5 which lists reported endogenous concentrations of cyanide in various biological samples from human smokers and non-smokers. Table 5 is disclosed in Textbook of Military Medicine, Chapter 11, 371-410.

Figure 8:
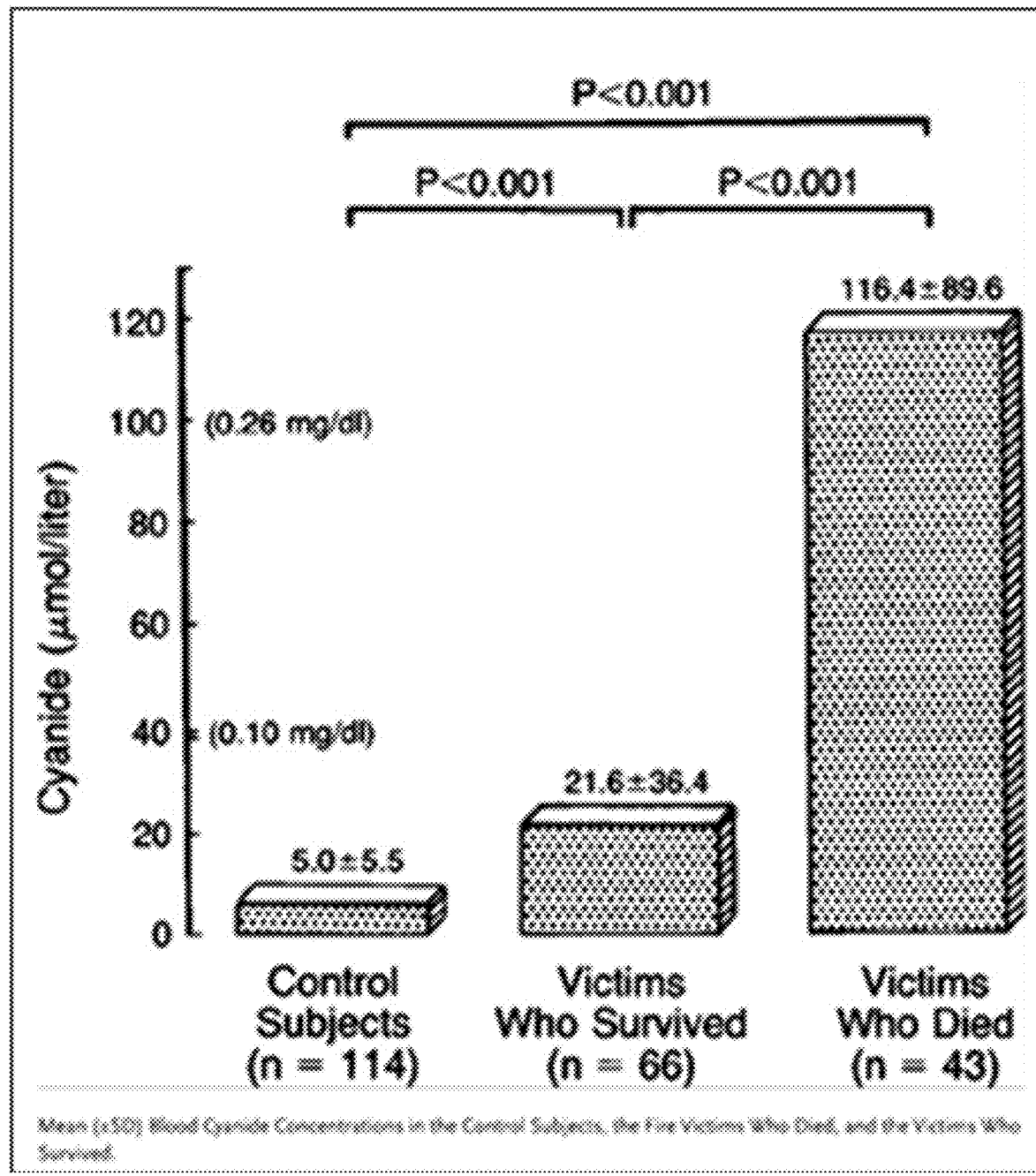
FIG. 8 illustrates the relationships of cyanide concentrations in blood of fire victims and controls.

A study in Paris withdrew blood from 109 victims of fire by the first medical team to reach the scene. Blood cyanide was measured and levels showed measurable differences between control subjects, victims who survived, and victims who died. FIG. 8 illustrates the mean (±SD) blood cyanide concentrations in the control subjects, the fire victims who died, and the victims who survived. Of the 109 fire victims from whom blood specimens were obtained, 43 died (39 percent). The mean blood cyanide concentration in these 109 patients was 59.0±77.9 µmol per liter. In those who died, it was 116.4±89.6 µmol per liter, and in those who survived it was 21.6±36.4 µmol per liter. All these values were significantly higher than those for the control group. The corresponding mean blood carbon monoxide concentration in the 109 fire victims was 1.5±1.7 mmol per liter. In those who died it was 2.8±2.0 mmol per liter, and in those who survived it was 0.7±0.7 mmol per liter. FIG. 8 is disclosed in Baud et. al., Elevated Blood Cyanide Concentrations in Victims of Smoke Inhalation, New England J. Medicine 325, 1761-1766 (1991).

The analytical determination of biological markers of cyanide exposure is not an easy task due to chemical properties, biological activities, and limited published research (for certain markers of cyanide exposure). Different approaches have their own advantages and disadvantages. For thiocyanate, the main drawback is large and variable background concentrations in biological samples. Other disadvantages include the conversion of cyanide and thiocyanate and the use of thiocyanate by other biological processes not directly related to cyanide metabolism.

Cyanide Exposure Detection Methodology

Figure 9:
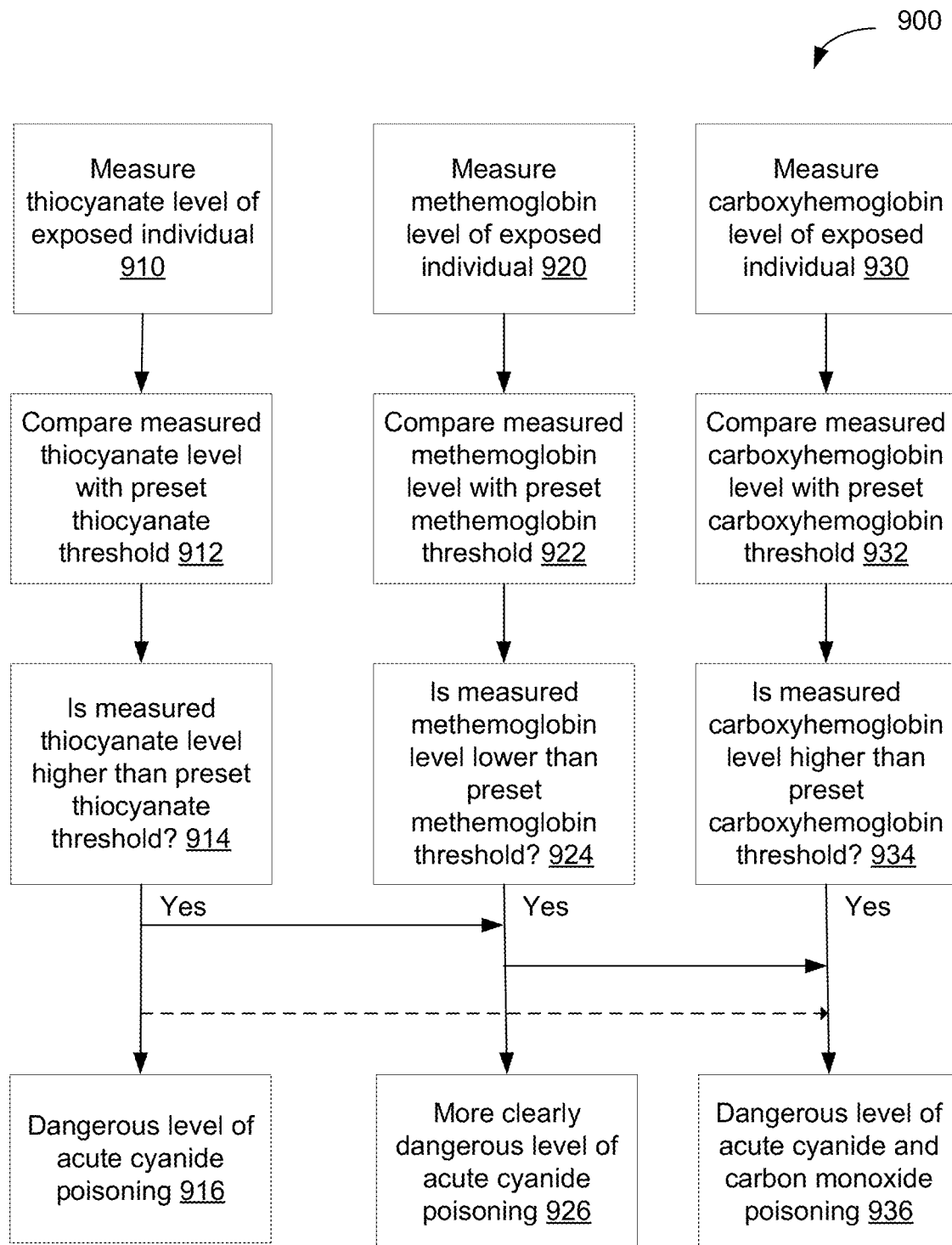
FIG. 9 shows an example of a flow diagram illustrating a method of detecting cyanide exposure.

FIG. 9 shows an example of a flow diagram 900 illustrating a method of detecting cyanide exposure. The method is based on measuring the presence or absence of elevated salivary thiocyanate and can be combined with measuring depressed methemoglobin values and/or with measuring elevated carboxyhemoglobin values. A fast, on-site, lifesaving test for cyanide intoxication in firefighters and smoke victims is presented.

First, the thiocyanate level is measured (step 910) to test for a high thiocyanate level above a preset thiocyanate threshold, which distinguishes between salivary thiocyanate levels of concern and levels not of concern. The comparison (912) and determination of an elevated thiocyanate level above the preset thiocyanate threshold (determination 914) leads to a conclusion of a dangerous level of acute cyanide poisoning (conclusion 916). That is, the result of the comparison indicates a level of acute cyanide poisoning for which medical treatment is recommended (and may be needed or required) to treat the health effects of the exposure. For instance, the exposed individual can use a simple chemical indicator (e.g., a swab or strip with a colorimetric indicator such as iron nitrate) to indicate the presence of a high thiocyanate level in saliva.

The thiocyanate measurement step 910 finds support in Table 2 in FIG. 2, which shows the results reported for students as a chemistry laboratory experiment based on using $Fe(NO_3)_3$ and reacting it with $SCN^-$:

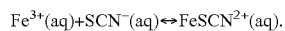

$$Fe^{3+}(aq) + SCN^-(aq) \leftrightarrow FeSCN^{2+}(aq).$$

The thiocyanoiron (II) ion is a deep red color that absorbs at 477 nm. A low-cost sample collection device (e.g., a swab or a strip) with a colorimetric indicator such as iron nitrate can be used to test for the presence of a high thiocyanate level in saliva.

Second, the methemoglobin level is measured to test for a low methemoglobin level below a preset methemoglobin threshold (step 920). The comparison (922) and determination of a depressed methemoglobin level below the preset methemoglobin threshold (determination 924), when combined with an elevated thiocyanate level above the preset thiocyanate threshold (determination 914), leads to a conclusion of a more clearly dangerous level of acute cyanide poisoning (conclusion 926). That is, a determination that the measured thiocyanate level is above the preset thiocyanate threshold and the measured methemoglobin level is below the preset methemoglobin threshold provides a more reliable or clearer or further indication of acute cyanide poisoning for which medical treatment is recommended to treat the health effects of the exposure. For instance, pulse oximetry can measure low methemoglobin to indicate that methemoglobin is no longer available to bind with cyanide in the exposed individual. A substantial reduction of methemoglobin in a cyanide exposed individual indicates that the capacity for conversion to thiosulfate has been exceeded. In one example, pulse oximetry involves the measurement of transmission of specific light frequencies across the finger or earlobe.

The first comparison determination of elevated salivary thiocyanate detection (determination 914) may be sufficient, and the second comparison determination of depressed methemoglobin detection (determination 924) may not be necessary. As discussed above, when analyzing for cyanide exposure, because all biological samples will contain endogenous levels of cyanide, some way of accounting for that is desirable in determining whether a sample contains a dangerous level of cyanide. The second comparison determination of depressed methemoglobin detection (determination 924) is used to take into account variations of endogenous levels of cyanide in different individuals so as to minimize or avoid false positives. Combined, these two measurements provide a more reliable basis or a further basis to indicate that the natural detoxification methods in the body are overwhelmed.

Third, the carboxyhemoglobin level is measured to test for exposure to CO (step 930). For instance, pulse oximetry can also be used to measure carboxyhemoglobin to assess the exposure to CO which could adjust the danger level of cyanide exposure. As discussed above, CO and HCN are the toxic twins of smoke inhalation. Even if the first and second comparison determinations indicate the absence of a dangerous level of cyanide exposure, the exposed individual may still be in danger due to CO exposure. The comparison (932) and determination of an elevated carboxyhemoglobin level above a preset carboxyhemoglobin threshold (determination 934), when combined with an elevated thiocyanate level above the preset thiocyanate threshold (determination 914) alone or further with a depressed methemoglobin level below the preset methemoglobin threshold (determination 924), leads to a conclusion of a dangerous level of acute cyanide and carbon monoxide poisoning (conclusion 936). That is, a determination that the measured thiocyanate level is above the preset thiocyanate threshold (with or without a determination that the measured methemoglobin level is below the preset methemoglobin threshold) and the measured carboxyhemoglobin level is above the preset carboxyhemoglobin threshold provides an indication of acute cyanide and carbon monoxide poisoning for which medical treatment is recommended to treat the health effects of the exposure for such harmed individuals. The third comparison determination of CO exposure level (determination 934) is used to further reduce the likelihood of death due to a combination of CO and cyanide poisoning.

Figure 10:
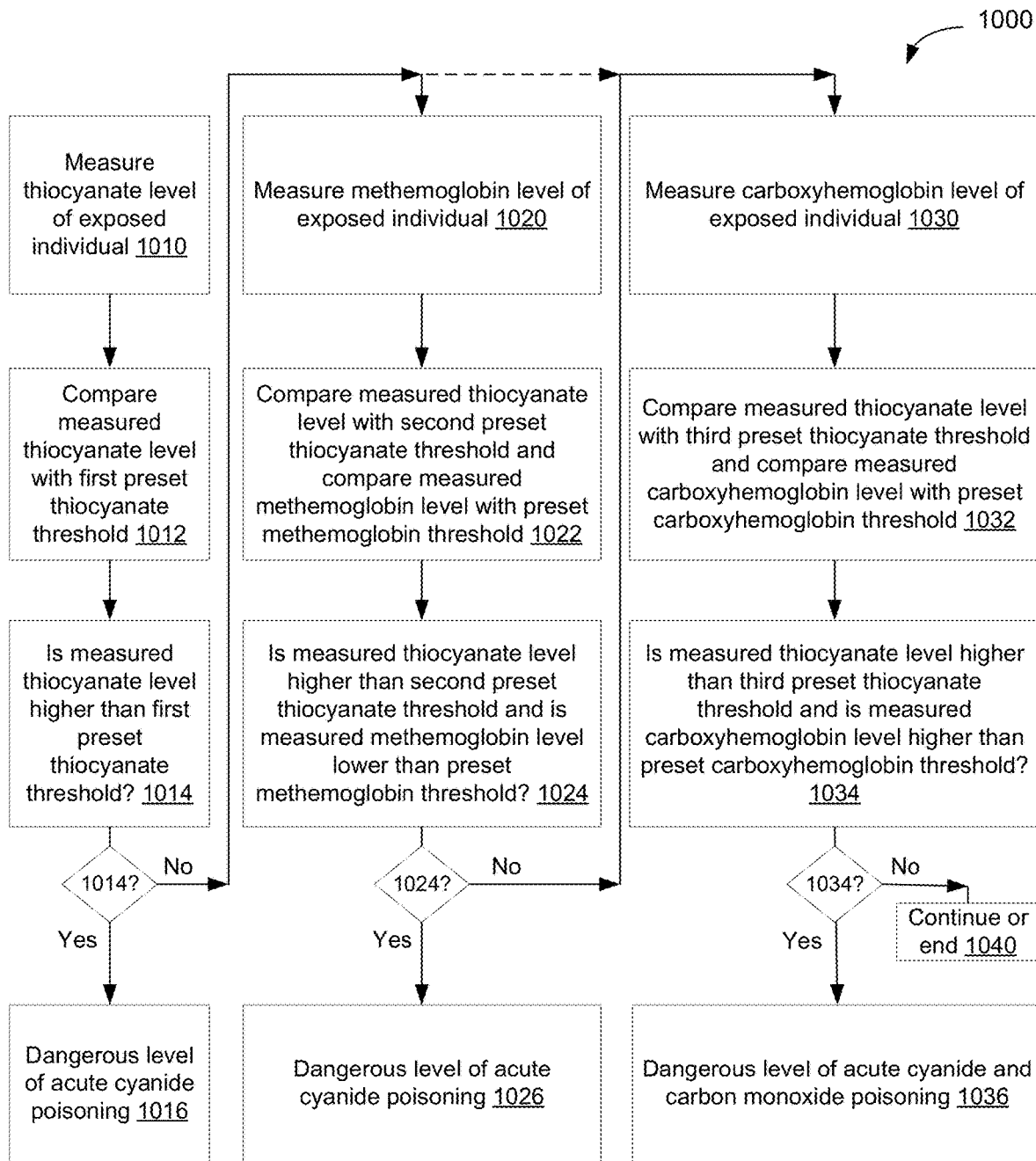
FIG. 10 shows an example of a flow diagram illustrating another method of detecting cyanide exposure.

FIG. 10 shows another example of a flow diagram 1000 illustrating another method of detecting cyanide exposure. The method is also based on measuring the presence or absence of elevated salivary thiocyanate and can be combined with measuring depressed methemoglobin values.

First, the thiocyanate level is measured (step 1010) to test for a high thiocyanate level above a first preset thiocyanate threshold, which distinguishes between salivary thiocyanate levels of concern and levels not of concern. The comparison (1012) and determination of an elevated thiocyanate level above the first preset thiocyanate threshold (determination 1014) leads to a conclusion of a dangerous level of acute cyanide poisoning (conclusion 1016). The thiocyanate measurement step 1010, comparison step 1012, and determination step 1014 may be similar to the thiocyanate measurement step 910, comparison step 912, and determination step 914, respectively.

Second, if the measured thiocyanate level does not reach above the first preset thiocyanate threshold in determination step 1014, the methemoglobin level is measured to test for a low methemoglobin level below a preset methemoglobin threshold (step 1020). Next, the method compares the measured thiocyanate level with a second preset thiocyanate threshold (which is lower than the first preset thiocyanate threshold) and compares the measured methemoglobin level with a preset methemoglobin threshold (step 1022). If it is determined that the measured thiocyanate level is higher than the second preset thiocyanate threshold and the measured methemoglobin level is lower than the preset methemoglobin threshold (determination 1024), it leads to the conclusion of a dangerous level of acute cyanide poisoning (conclusion 1026) for which medical treatment is recommended (or needed) to treat the health effects of the exposure.

Third, if (i) the measured thiocyanate level does not reach above the first preset thiocyanate threshold in determination step 1014, or (ii) it is determined in step 1024 that the measured thiocyanate level is not higher than the second preset thiocyanate threshold and/or the measured methemoglobin level is not lower than the preset methemoglobin threshold, the carboxyhemoglobin level is measured to test for exposure to CO (step 1030). Next, the method compares the measured thiocyanate level with a third preset thiocyanate threshold (which is lower than the first preset thiocyanate threshold and may be the same as or different from the second preset thiocyanate threshold) and compares the measured carboxyhemoglobin level with a preset carboxyhemoglobin threshold (1032). If it is determined that the measured thiocyanate level is above the third preset thiocyanate threshold and the measured carboxyhemoglobin level is higher than the preset carboxyhemoglobin threshold (determination 1034), it leads to a conclusion of a dangerous level of acute cyanide and carbon monoxide poisoning (conclusion 1036). If not, the process continues with the measuring and comparing or ends (1040).

Cyanide Exposure Detection Device

Thiocyanate is relatively non-toxic and concentrates in the saliva. An aspect of the detection methodology is based on the rapid and reliable determination of thiocyanate in saliva using a photometric method. When Fe(III) ions are added to samples containing thiocyanate, a red complex is formed, which is measured close to its absorption maximum at 492 nm. The photometric method permits the quantitative determination of thiocyanate in small sample volumes and with a short sample preparation time. In one example, a saliva sample from a potentially exposed person can be placed in contact with a simple chemical indicator that will indicate, in conjunction with pulse oximetry measurements, whether or not a high-level cyanide exposure has occurred. A low-cost sample collection device with a colorimetric indicator such as iron nitrate can be used to test for the presence of a high thiocyanate level in saliva. An example utilizes metal surfaces for detecting cyanide and related species, as disclosed in U.S. Pat. No. 7,776,610, which is incorporated herein by reference in its entirety.

Another example involves the use of test strips which are covered on two sides by parafilm. The operator would peel open the parafilm to expose the test strip. As used herein, the term "strip" is not limited to a rectangular strip but may have any shape including a circular shape similar to that of a standard hole punch. Such a circle is the size of the test substrate suitable for the test, among other examples that include rectangular and square test substrates. Saliva is a prime candidate as a test sample. The present disclosure is not limited to saliva. Suitable test samples may include blood or other bodily fluids.

Color Calibration Curve

Establishing a calibration curve is an aspect of implementing the cyanide detection methodology using a cyanide exposure detection device that can be deployed to the front line to detect thiocyanate levels in front line workers such as firefighters and others such as fire smoke victims on-scene.

One way of establishing the calibration curve employs the Pena-Pereira approach. It may use the following materials: 1M nitric acid, 1M thiocyanate solution, iron nitrate, artificial saliva (or distilled water if artificial saliva is not available), Whatman #1 filter paper (Nitrocellulose based), roughly 35 mm$^2$ sample substrates from the filter paper, either using a ¼-in hole punch or Pena-Pereira's method of using ink gel pens to block off areas (e.g., 6-mm squares), 2 µL pipette, and a camera.

An experiment may be carried out in accordance with Pena-Pereira except as noted. The user may prepare various thiocyanate concentration solutions and prepare 10 sample substrate filter papers per each thiocyanate solution (for statistical analysis). The user may add thiocyanate solutions to the prepared filter substrates and record the color change with the camera after periods ranging from about 5 minutes to 2 weeks. The user can then use the image analysis algorithm to analyze the captures images (i.e., Photometrix®). Based on the analysis, the user can establish a dose-color response calibration curve of thiocyanate concentration.

Figure 11:
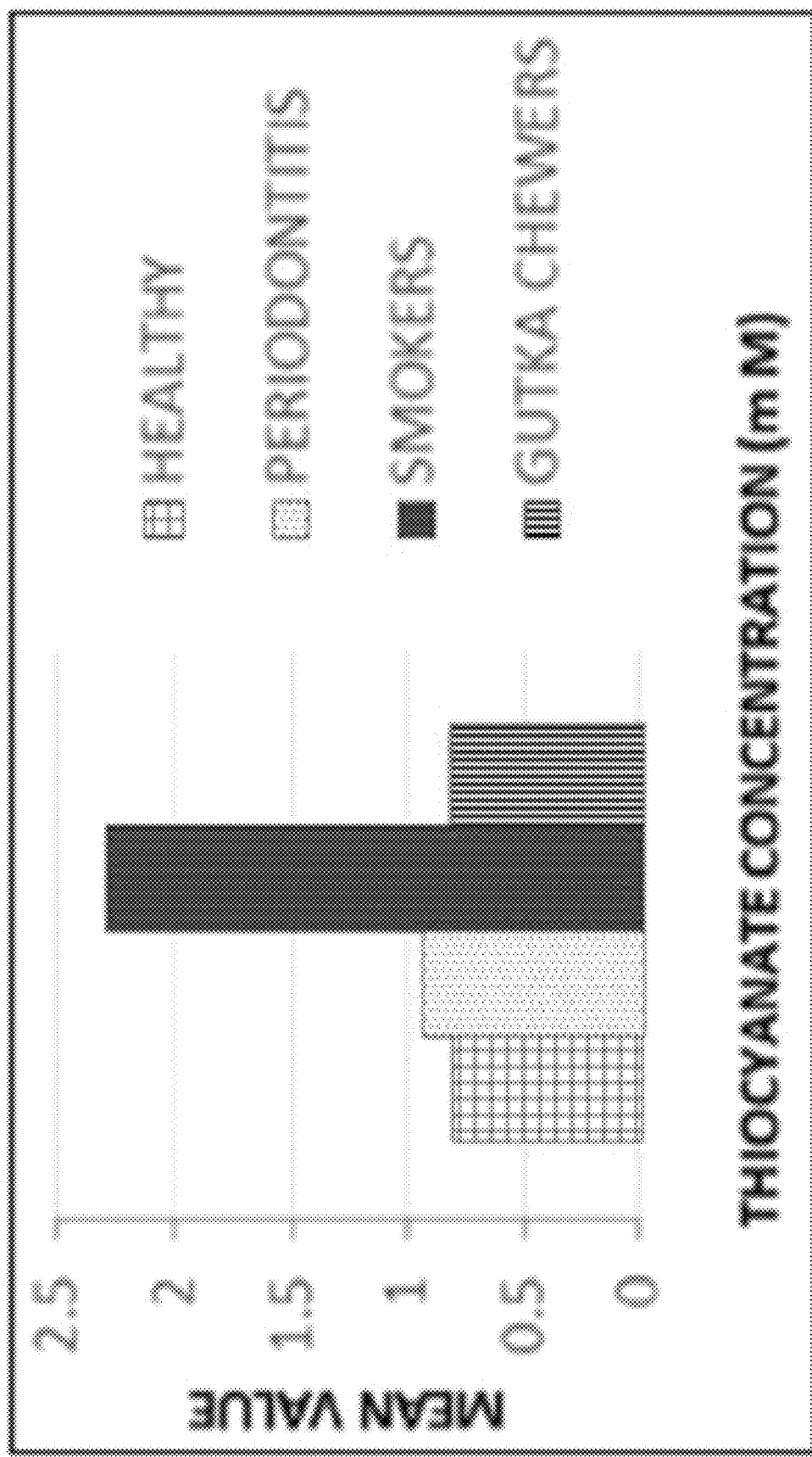
FIG. 11 shows an example of a salivary thiocyanate levels generated for four groups: Healthy, Periodontitis, Smokers, and Gutka chewers.

FIG. 11 shows an example of salivary thiocyanate levels generated for a different context by Shashikanth Hegde et al., Estimation and correlation of salivary thiocyanate levels in periodontally healthy subjects, smokers, nonsmokers, and gutka-chewers with chronic periodontitis, Indian J. Dent. Res. 2016; 27:12-4. The bar chart in FIG. 11 shows the thiocyanate concentration for four groups (healthy, periodontitis, smokers, and gutka chewers) not related to smoke inhalation.

Figure 12:
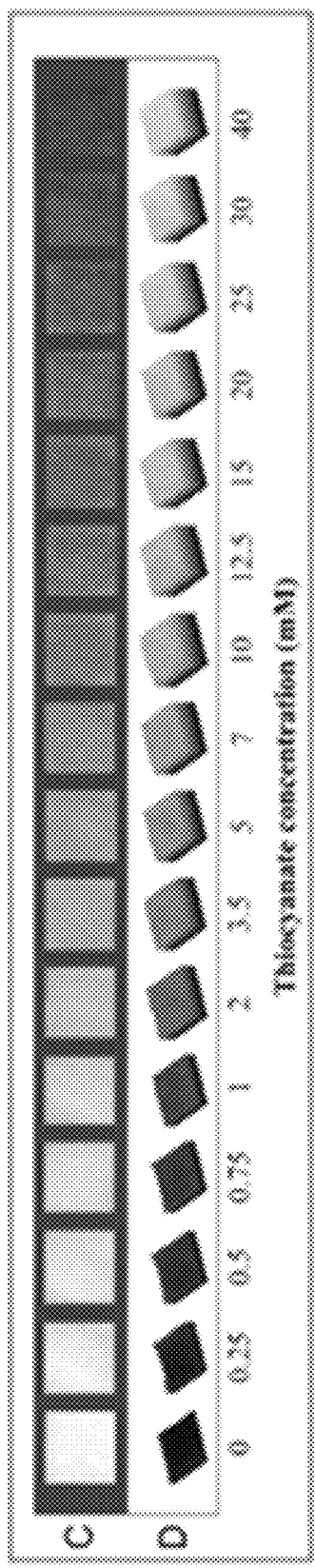
FIG. 12 shows the degree of color change with different concentrations of thiocyanate according to one example.

FIG. 12 shows the degree of color change with different concentrations of thiocyanate according to one example taken from Pena Pereira et al., Paper-Based Analytical Device for Instrumental-Free Detection of Thiocyanate in Saliva as a Biomarker of Tobacco Smoke Exposure 2016, Talanta, January 15 147. Measuring thiocyanate in saliva can be easily and cheaply determined by contacting saliva with iron nitrate on a test strip. The test strip turns red. The degree of red depends on thiocyanate concentration. The darker the red, the higher the level of thiocyanate indicating how much cyanide has been removed from the blood stream.

A calibration can be achieved by testing and detecting a potential range of thiocyanate concentration after fire smoke exposure. If the thiocyanate level in saliva rises high enough and fast enough, and stays elevated long enough, and if sufficient distinction can be made between the non-exposed general population's expected range of thiocyanate concentration and levels shown by individuals exposed to cyanide smoke, and if further medical monitoring can determine what level shows no significant harm to the body, then an action level can be determined and the test will be successful.

Figure 13:
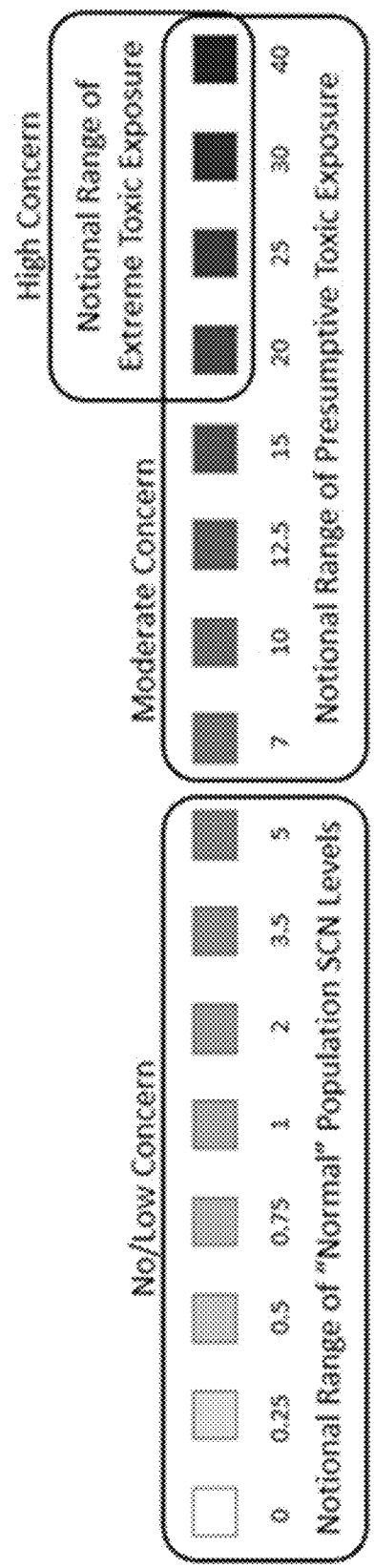
FIG. 13 shows notional different categories of concern based on the degree of color change with different concentrations of thiocyanate.

FIG. 13 shows notional different categories of concern based on the degree of color change with different concentrations of thiocyanate. Some thiocyanate values will be of low concern because they are in a range normally exhibited by the population. Some concentrations will be higher than that but of moderate concern. It is expected that some of these levels of thiocyanate would not produce noticeable harmful effects. The highest levels would be of high concern because they indicate a potential for severe health impacts. Field testing research over time will allow levels of concern to be more definitively determined.

Stability of Sampling Substrate

To test the stability of the sampling substrate, the user may employ the following process. In the above experiment, the user may vary the time between substrate preparation and adding the thiocyanate from about 5 minutes to 2 weeks. The user may store the prepared substrates in plastic zip bags (i.e., zip-top bags) at room temperature between preparation and reuse. If the user observes a change, then the user records the degradation of color change with time (e.g., up to about 30 minutes). This is not considered critical for the testing because it is anticipated that the testers will record the results immediately. If the user does not observe a change, this step is skipped. Next, if the results vary as expected in the first test, the user may try different approaches such as sealing the substrate or considering the use of stabilizers. This will not need to be extensive because the user can perform the field tests by having the EMT (emergency medical technician) or the like add the indicator solution before use (although this is less than optimum).

Sample Collection

For the purpose of field testing, test subjects may be requested to expectorate into a small weigh boat saliva sample and then 2 μL aliquot may be drawn. Validating this will not occur in the lab until human subject testing considerations are addressed or a laboratory within national laboratories that can perform such testing is found.

Production

Collected experimental data and conditions may be used to guide the production of robust and durable test kits which will be deployed for cyanide poisoning detection. A number of test substrates would be packaged in accordance with the process for testing the stability of the sampling substrate as described above. The packaged test substrates can then be individually used by trained testers (e.g., EMTs).

Field Testing

The field testing may involve collecting thiocyanate samples from a plurality of test individuals. Examples of test individuals include firefighters before and after fire smoke exposure and thiocyanate samples from fire smoke inhalation victims as well as unexposed individuals. The goal is to identify a threshold level of thiocyanate or threshold thiocyanate level that indicates a cyanide exposure at which medical attention is recommended. That level can be well above the normal levels seen in the general population, making it less likely that medical attention would be sought that turned out not to be necessary. Additionally, there may be levels that will be above normal levels in the population but below health hazard levels. The field testing will help identify this acceptable level that is below health hazard levels for which there is low to no concern. This may involve a subject whose body is still relying on the reserve thiocyanate detoxification. As such, there may be three levels in the color change illustrated in FIG. 13. The (first) normal low levels are really of low/no concern since the general population all have such levels of thiocyanate anyway. The (second) moderate concern levels will be in that range where the thiocyanate is still detoxifying the body but is above normal levels. It is not known whether those moderate levels are not producing some effects. They may not merely be of low/no concern. The (third) high levels are where damage can start and these would be actionable.

The field test may involve creating test strips that can be sent to the field, collecting samples, and applying to the test strip for firefighters before and after a fire and victims after being exposed. Initially multiple post-exposure tests over time can be performed to characterize the thiocyanate levels changing. The field test may further involve recording the concentration of thiocyanate, monitoring outcomes for these firefighters and victims to relate thiocyanate levels with health effects, and based on the data, determining if an action level, indicating further monitoring or treatment is recommended, can be defined. The field testing may conclude with identifying the threshold level of thiocyanate that indicates a cyanide exposure at which medical attention is recommended. The identified threshold thiocyanate level can be set as the preset thiocyanate threshold. The testing device or test kit can be used for field use to test potentially dangerous levels of cyanide exposure based on the predetermined threshold levels. Test results may be quite immediate, and the potentially poisoned individual can be promptly sent for further medical tests and treatment.

Field testing details may be determined with the testing organization such as a municipal fire department. In one example, the firefighters will have saliva tested before and after working an active fire. To establish thiocyanate timelines, samples may be taken and tested as soon as possible after the fire and then 3 further tests at 15-minute intervals. The time for intervals may be adjusted as the data warrants. If possible, the victims would also be tested as soon as possible and then at similar time intervals. The length of the time intervals is not critical as long as it is recorded. The thiocyanate level of the individual is measured after the individual is exposed to cyanide at a time of exposure, multiple times at different time intervals from the time of exposure, and the measured thiocyanate level at each of the multiple times is compared to the preset thiocyanate threshold.

After each test, an image may be made to record the color change and relevant data pertaining to the individual. The individual's name does not need to be disclosed. In addition to thiocyanate values, measurement of methemoglobin using a multi-channel pulse oximeter may be performed to monitor any changes as cyanide is detoxified and determine if a correlation exists. If a firefighter or victim is judged to be cyanide intoxicated, if possible, medical center data such as methemoglobin or blood cyanide levels may be recorded. All data will be collected to facilitate data analysis to determine thiocyanate action levels.

Front line Detection of Cyanide Exposure

After determining the preset threshold values (including the preset thiocyanate threshold or first, second, and third preset thiocyanate thresholds for the first comparison determination of FIGS. 9 and 10, respectively, the preset methemoglobin threshold for the second comparison determination of FIGS. 9 and 10, and the preset carboxyhemoglobin threshold of FIGS. 9 and 10), the cyanide exposure detection device can be deployed to the front line to test thiocyanate levels in front line workers such as firefighters and others such as fire smoke victims on-scene.

The thiocyanate level of the individual may be measured after the individual is exposed to cyanide at a time of exposure, multiple times at different time intervals from the time of exposure, and the measured thiocyanate level at each of the multiple times is compared to the preset thiocyanate threshold. This takes into account any changing values of the thiocyanate level over time after the exposure.

Similarly, the methemoglobin level of the individual may be measured after the individual is exposed to cyanide at the time of exposure, multiple times at different intervals from the time of exposure, and the measured methemoglobin level at each of the multiple times is compared to the preset methemoglobin threshold. This takes into account any changing values of the methemoglobin level over time after the exposure.

The inventive concepts taught by way of the examples discussed above are amenable to modification, rearrangement, and embodiment in several ways. For example, different ways of measuring thiocyanate, methemoglobin, and carboxyhemoglobin levels from those described herein can be used.

Accordingly, although the present disclosure has been described with reference to specific embodiments and examples, persons skilled in the art will recognize that changes may be made in form and detail without departing from the spirit and scope of the disclosure.

The claims define the invention and form part of the specification. Limitations from the written description are not to be read into the claims.

An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features and/or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not to be taken as limiting or restricting the systems, techniques, approaches, methods, devices to those appearing in any section. Rather, the teachings and disclosures herein can be combined, rearranged, with other portions of this disclosure and the knowledge of one of ordinary skill in the art. It is the intention of this disclosure to encompass and include such variation. The indication of any elements or steps as "optional" does not indicate that all other or any other elements or steps are mandatory.

What is claimed is:

1. A method of detecting cyanide exposure of an individual, the method comprising measuring a thiocyanate level of the individual which includes measuring thiocyanate ($SCN^-$) catalyzed by enzyme rhodanese of the individual; determining a preset thiocyanate threshold; and comparing the measured thiocyanate level to the preset thiocyanate threshold to determine whether the measured thiocyanate level is above the preset thiocyanate threshold indicating a level of cyanide poisoning for which medical treatment is recommended to treat health effects of the exposure, wherein determining the preset thiocyanate threshold includes:
    measuring thiocyanate levels of a plurality of test individuals after an exposure of the plurality of test individuals to cyanide;
    measuring thiocyanate levels of at least some of the plurality of test individuals before the exposure of the plurality of test individuals to cyanide;
    monitoring the plurality of test individuals after the exposure for health effects of the exposure;
    identifying, out of the plurality of test individuals being monitored, one or more harmed individuals for whom medical treatment is recommended to treat the health effects of the exposure;
    comparing the thiocyanate levels of the at least some of the plurality of test individuals before the exposure, the thiocyanate levels of the one or more harmed individuals, and the thiocyanate levels of the plurality of test individuals after the exposure who are not the one or more harmed individuals;
    determining, based on the comparing, a threshold thiocyanate level above which medical treatment is recommended to treat the health effects of the exposure; and
    setting the threshold thiocyanate level as the preset thiocyanate threshold.

2. The method of claim 1, wherein comparing the measured thiocyanate level to the preset thiocyanate threshold comprises:
    comparing the measured thiocyanate level to the preset thiocyanate threshold to determine whether the measured thiocyanate level is above the preset thiocyanate threshold indicating the level of cyanide poisoning for which it is recommended to perform at least one of medical screening, testing, monitoring, or treating the individual.

3. The method of claim 1, wherein comparing the measured thiocyanate level to the preset thiocyanate threshold comprises:
    comparing the measured thiocyanate level to the preset thiocyanate threshold to determine whether the measured thiocyanate level is above the preset thiocyanate threshold indicating the level of cyanide poisoning for which administering an antidote is recommended.

4. The method of claim 1, comparing the measured thiocyanate level to the preset thiocyanate threshold comprises:
    comparing the measured thiocyanate level to the preset thiocyanate threshold to determine whether the measured thiocyanate level is above the preset thiocyanate threshold indicating the level of cyanide poisoning for which administering a nitrite based antidote is recommended.

5. The method of claim 1, wherein measuring the thiocyanate level comprises:
    placing a biological fluid of the individual in contact with a chemical indicator to measure the thiocyanate level.

6. The method of claim 5,
    wherein the biological fluid comprises saliva.

7. The method of claim 6,
wherein the saliva is collected using a swab or a strip.

8. The method of claim 6,
wherein the saliva is expectorated into a collection device and a preset amount transferred onto a prepared indicator substrate.

9. The method of claim 8,
wherein the preset amount of approximately 2 µL saliva is transferred onto the prepared indicator substrate with a pipette.

10. The method of claim 8,
wherein the preset amount of approximately 1 µL to 3 µL saliva is transferred onto the prepared indicator substrate with a pipette.

11. The method of claim 10, wherein measuring the thiocyanate level comprises:
placing a biological fluid of the individual in contact with a chemical indicator to measure the thiocyanate level, wherein the biological fluid comprises saliva.

12. The method of claim 11,
wherein the saliva is collected using a swab or a strip.

13. The method of claim 11,
wherein the saliva is expectorated into a collection device and a preset amount transferred onto a prepared indicator substrate.

14. The method of claim 11,
wherein the preset amount of approximately 2 µL saliva is transferred onto the prepared indicator substrate with a pipette.

15. The method of claim 5,
wherein the chemical indicator comprises a colorimetric indicator.

16. The method of claim 15,
wherein the colorimetric indicator comprises iron nitrate.

17. The method of claim 1,
wherein the thiocyanate level of the individual is measured after the individual is exposed to cyanide at a time of exposure, multiple times at different time intervals from the time of exposure, and the measured thiocyanate level at each of the multiple times is compared to the preset thiocyanate threshold.

18. A method of detecting cyanide exposure of an individual, the method comprising measuring a thiocyanate level of the individual; determining a preset thiocyanate threshold; and comparing the measured thiocyanate level to the preset thiocyanate threshold to determine whether the measured thiocyanate level is above the preset thiocyanate threshold indicating a level of cyanide poisoning requiring medical assessment, wherein determining the preset thiocyanate threshold includes:
measuring thiocyanate levels of a plurality of test individuals after an exposure of the plurality of test individuals to cyanide;
measuring thiocyanate levels of at least some of the plurality of test individuals before the exposure of the plurality of test individuals to cyanide;
monitoring the plurality of test individuals after the exposure for health effects of the exposure;
identifying, out of the plurality of test individuals being monitored, one or more harmed individuals for whom medical assessment is required;
comparing the thiocyanate levels of the at least some of the plurality of test individuals before the exposure, the thiocyanate levels of the one or more harmed individuals, and the thiocyanate levels of the plurality of test individuals after the exposure who are not the one or more harmed individuals;
determining, based on the comparing, a threshold thiocyanate level above which medical assessment is required; and
setting the threshold thiocyanate level as the preset thiocyanate threshold.

19. The method of claim 18,
wherein the thiocyanate levels of the plurality of test individuals, after the exposure at a time of exposure, are measured multiple times at different time intervals from the time of exposure, and the measured thiocyanate levels including the thiocyanate levels measured at the different time intervals after the time of exposure are compared.

20. The method of claim 18, wherein determining the preset thiocyanate threshold further includes:
measuring thiocyanate levels of a plurality of unexposed individuals who have not been exposed to cyanide;
comparing the thiocyanate levels of the at least some of the plurality of test individuals before the exposure, the thiocyanate levels of the one or more harmed individuals, the thiocyanate levels of the plurality of test individuals after the exposure who are not the one or more harmed individuals, and the thiocyanate levels of the plurality of unexposed individuals;
determining, based on the comparing, the threshold thiocyanate level above which medical assessment is required; and
setting the threshold thiocyanate level as the preset thiocyanate threshold.

21. A method of detecting cyanide exposure of an individual, the method comprising:
measuring a thiocyanate level of the individual which comprises measuring rhodanide as a main metabolite of cyanide to be used as biomarker for exposure to cyanide or to cyanide releasing chemicals;
comparing the measured thiocyanate level to a first preset thiocyanate threshold to determine whether the measured thiocyanate level is above the first preset thiocyanate threshold;
if the measured thiocyanate level is above the first preset thiocyanate threshold, performing medical assessment of the individual;
if the measured thiocyanate level is not above the first preset thiocyanate threshold, then performing at least one of
(i) measuring a methemoglobin level of the individual, comparing the measured thiocyanate level to a second preset thiocyanate threshold, which is lower than the first preset thiocyanate threshold, to determine whether the measured thiocyanate level is above the second preset thiocyanate threshold, comparing the measured methemoglobin level to a preset methemoglobin threshold to determine whether the measured methemoglobin level is below the preset methemoglobin threshold, and if the measured thiocyanate level is above the second preset thiocyanate threshold and the measured methemoglobin level is below the preset methemoglobin threshold, performing medical assessment of the individual; or
(ii) measuring a carboxyhemoglobin level of the individual, comparing the measured thiocyanate level to a third preset thiocyanate threshold, which is lower than the first preset thiocyanate threshold, to determine whether the measured thiocyanate level is above the third preset thiocyanate threshold, comparing the measured carboxyhemoglobin level with a preset carboxyhemoglobin threshold to determine whether the measured carboxyhemoglobin level is above the preset carboxyhemoglobin threshold, and if the measured thiocyanate level is above the third preset thiocyanate threshold and the measured carboxyhemoglobin level is above the preset carboxyhemoglobin threshold, performing medical assessment of the individual.

22. The method of claim 21, wherein if the measured thiocyanate level is not above the first preset thiocyanate threshold:
measuring a methemoglobin level of the individual, comparing the measured thiocyanate level to a second preset thiocyanate threshold, which is lower than the first preset thiocyanate threshold, to determine whether the measured thiocyanate level is above the second preset thiocyanate threshold, comparing the measured methemoglobin level to a preset methemoglobin threshold to determine whether the measured methemoglobin level is below the preset methemoglobin threshold, and if the measured thiocyanate level is above the second preset thiocyanate threshold and the measured methemoglobin level is below the preset methemoglobin threshold, performing medical assessment of the individual;
if the measured thiocyanate level is not above the first preset thiocyanate threshold or if the measured methemoglobin level is not below the preset methemoglobin threshold, measuring a carboxyhemoglobin level of the individual, comparing the measured thiocyanate level to a third preset thiocyanate threshold, which is lower than the first preset thiocyanate threshold, to determine whether the measured thiocyanate level is above the third preset thiocyanate threshold, comparing the measured carboxyhemoglobin level with a preset carboxyhemoglobin threshold to determine whether the measured carboxyhemoglobin level is above the preset carboxyhemoglobin threshold, and if the measured thiocyanate level is above the third preset thiocyanate threshold and the measured carboxyhemoglobin level is above the preset carboxyhemoglobin threshold, performing medical assessment of the individual.

23. The method of claim 21,
wherein the thiocyanate level of the individual is measured after the individual is exposed to cyanide at a time of exposure, multiple times at different time intervals from the time of exposure, and the measured thiocyanate level at each of the multiple times is compared to at least the first preset thiocyanate threshold among the first, second, and third preset thiocyanate thresholds.

24. The method of claim 21,
wherein the methemoglobin level of the individual is measured after the individual is exposed to cyanide at a time of exposure, multiple times at different intervals from the time of exposure, and the measured methemoglobin level at each of the multiple times is compared to the preset methemoglobin threshold.

25. A method of detecting cyanide exposure of an individual, the method comprising:
determining a preset thiocyanate threshold;
measuring a thiocyanate level of the individual, which comprises measuring thiocyanate (SCN⁻) catalyzed by enzyme rhodanese of the individual as follows

and comparing the measured thiocyanate level to the preset thiocyanate threshold to determine whether the measured thiocyanate level is above the preset thiocyanate threshold indicating a level of cyanide poisoning requiring medical assessment;
determining the preset thiocyanate threshold including:
measuring thiocyanate levels of a plurality of unexposed individuals who have not been exposed to cyanide;
measuring thiocyanate levels of a plurality of exposed individuals after an exposure of the plurality of exposed individuals to cyanide;
monitoring the plurality of exposed individuals after the exposure for health effects of the exposure;
identifying, out of the plurality of exposed individuals being monitored, one or more harmed individuals for whom medical assessment is required;
comparing thiocyanate levels of the plurality of unexposed individuals, thiocyanate levels of the one or more harmed individuals, and thiocyanate levels of the plurality of exposed individuals after the exposure who are not the one or more harmed individuals;
determining, based on the comparing, a threshold thiocyanate level above which medical assessment is required; and
setting the threshold thiocyanate level as the preset thiocyanate threshold.

26. The method of claim 25,
wherein the thiocyanate levels of the plurality of exposed individuals, after the exposure at a time of exposure, are measured multiple times at different time intervals from the time of exposure, and the measured thiocyanate levels including the thiocyanate levels measured at the different time intervals after the time of exposure are compared.

27. The method of claim 25,
wherein the plurality of exposed individuals include at least some of the plurality of unexposed individuals before the exposure who become exposed individuals after the exposure.

28. The method of claim 25, wherein measuring the thiocyanate level comprises:
placing a biological fluid of the individual in contact with a chemical indicator to measure the thiocyanate level.

29. A method of detecting cyanide exposure of an individual, the method comprising:
determining a preset thiocyanate threshold;
measuring a thiocyanate level of the individual which includes measuring rhodanide as a main metabolite of cyanide to be used as biomarker for exposure to cyanide or to cyanide releasing chemicals; and
comparing the measured thiocyanate level to a preset thiocyanate threshold to determine whether the measured thiocyanate level is above the preset thiocyanate threshold indicating a level of cyanide poisoning for which medical treatment is recommended to treat health effects of the exposure; and
determining the preset thiocyanate threshold including:
measuring thiocyanate levels of a plurality of unexposed individuals who have not been exposed to cyanide;
measuring thiocyanate levels of a plurality of exposed individuals after an exposure of the plurality of exposed individuals to cyanide;
monitoring the plurality of exposed individuals after the exposure for health effects of the exposure;
identifying, out of the plurality of exposed individuals being monitored, one or more harmed individuals for whom medical treatment is recommended to treat the health effects of the exposure;

comparing thiocyanate levels of the plurality of unexposed individuals, thiocyanate levels of the one or more harmed individuals, and thiocyanate levels of the plurality of exposed individuals after the exposure who are not the one or more harmed individuals;

determining, based on the comparing, a threshold thiocyanate level above which medical treatment is recommended to treat the health effects of the exposure; and setting the threshold thiocyanate level as the preset thiocyanate threshold.

30. The method of claim 29, wherein the comparing comprises:

comparing the measured thiocyanate level to the preset thiocyanate threshold to determine whether the measured thiocyanate level is above the preset thiocyanate threshold indicating the level of cyanide poisoning for which timely administration of an antidote is recommended to rescue the individual.

31. The method of claim 29, wherein comparing the measured thiocyanate level to the preset thiocyanate threshold comprises:

comparing the measured thiocyanate level to the preset thiocyanate threshold to determine whether the measured thiocyanate level is above the preset thiocyanate threshold indicating the level of cyanide poisoning which is a potentially lethal exposure of cyanide for the individual.

* * * * *